(12) United States Patent
Murphy et al.

(10) Patent No.: US 11,992,271 B2
(45) Date of Patent: *May 28, 2024

(54) SURGICAL SYSTEM USING A REGISTRATION DEVICE

(71) Applicant: Stephen B. Murphy, Winchester, MA (US)

(72) Inventors: Stephen B. Murphy, Winchester, MA (US); William S. Murphy, Winchester, MA (US)

(73) Assignee: Stephen B. Murphy, Winchester, MA (US)

( * ) Notice: Subject to any disclaimer, the term of this patent is extended or adjusted under 35 U.S.C. 154(b) by 679 days.

This patent is subject to a terminal disclaimer.

(21) Appl. No.: 16/430,710

(22) Filed: Jun. 4, 2019

(65) Prior Publication Data

US 2019/0314091 A1 Oct. 17, 2019

Related U.S. Application Data

(60) Continuation of application No. 13/764,637, filed on Feb. 11, 2013, now Pat. No. 10,335,236, which is a
(Continued)

(51) Int. Cl.
*A61B 34/20* (2016.01)
*A61B 34/00* (2016.01)

(52) U.S. Cl.
CPC .............. *A61B 34/20* (2016.02); *A61B 34/70* (2016.02)

(58) Field of Classification Search
CPC .......... A61B 34/20; A61B 34/30; A61B 34/70
See application file for complete search history.

(56) References Cited

U.S. PATENT DOCUMENTS

| 3,457,651 A | 7/1969 | Kaeck |
| 5,056,523 A | 10/1991 | Hotchkiss, Jr. et al. |

(Continued)

FOREIGN PATENT DOCUMENTS

| DE | 19521060 A1 | 12/1996 |
| DE | 102004010332 B3 | 10/2005 |

(Continued)

OTHER PUBLICATIONS

European Search Report, European Application No. 13153277.2-1659 / 2626032, Applicant: Stephen B. Murphy, dated Mar. 20, 2014, pp. 1-6.

(Continued)

*Primary Examiner* — Si Ming Ku
(74) *Attorney, Agent, or Firm* — Cesari and McKenna, LLP

(57) ABSTRACT

A system and method creates a patient-specific surgical plan for use during a surgical procedure. The plan may reference an instrument for registering a portion of a patient during the procedure. The plan may be based on a computer-generated model of a portion of the patient's anatomy. The plan may be provided to a surgeon who uses the registration instrument to register the portion of the patient's anatomy according to the plan. Spatial location data for a plurality of points on the instrument and/or on the patient's anatomy may be obtained, and a patient-based coordinate system may be established using the registration instrument, the captured spatial location data or combinations thereof. The coordinate system may be used to attach one or more prosthetic components to the patient at locations and/or orientations specified in the plan.

25 Claims, 13 Drawing Sheets

Related U.S. Application Data continuation-in-part of application No. 13/537,654, filed on Jun. 29, 2012, now Pat. No. 9,101,378, which is a division of application No. 12/134,545, filed on Jun. 6, 2008, now Pat. No. 8,267,938.

(60) Provisional application No. 61/597,289, filed on Feb. 10, 2012, provisional application No. 60/984,425, filed on Nov. 1, 2007.

(56) References Cited

U.S. PATENT DOCUMENTS

| | | | |
|---|---|---|---|
| 5,086,401 | A | 2/1992 | Glassman |
| 5,122,145 | A | 6/1992 | Fishbane |
| 5,127,920 | A | 7/1992 | MacArthur |
| 5,141,512 | A | 8/1992 | Farmer et al. |
| 5,141,513 | A | 8/1992 | Fortune et al. |
| 5,320,625 | A | 6/1994 | Bertin |
| 5,327,907 | A | 7/1994 | Fischer |
| 5,376,093 | A | 12/1994 | Newman |
| 5,515,616 | A | 5/1996 | Merkin |
| 5,571,111 | A | 11/1996 | Aboczky |
| 5,697,939 | A | 12/1997 | Kubota et al. |
| 5,776,143 | A | 7/1998 | Adams |
| 5,824,007 | A | 10/1998 | Faraz et al. |
| 5,916,219 | A | 6/1999 | Matsuno et al. |
| 6,090,114 | A | 7/2000 | Matsuno et al. |
| 6,132,437 | A | 10/2000 | Omurtag et al. |
| 6,228,089 | B1 | 5/2001 | Wahrburg |
| 6,273,891 | B1 | 8/2001 | Masini |
| 6,290,196 | B1 | 9/2001 | Mayenberger |
| 6,314,312 | B1 | 11/2001 | Wessels |
| 6,395,005 | B1 | 5/2002 | Lovell |
| 6,482,237 | B2 | 11/2002 | Mosseri |
| 6,634,883 | B2 | 10/2003 | Ranalli |
| 6,743,235 | B2 | 6/2004 | Subba Rao |
| 7,090,677 | B2 | 8/2006 | Fallin et al. |
| 7,182,766 | B1 | 2/2007 | Mogul |
| 7,201,756 | B2 | 4/2007 | Ross et al. |
| 7,344,542 | B2 | 3/2008 | Coliazo et al. |
| 7,419,492 | B2 | 9/2008 | Yoon et al. |
| 7,651,501 | B2 | 1/2010 | Penenberg et al. |
| 7,780,672 | B2 | 8/2010 | Metzger et al. |
| 7,885,705 | B2 | 2/2011 | Murphy |
| 8,267,938 | B2 | 9/2012 | Murphy |
| 8,986,309 | B1 | 3/2015 | Murphy |
| 9,101,378 | B2 | 8/2015 | Murphy |
| 9,101,431 | B2 | 8/2015 | Murphy |
| 9,474,470 | B2 | 10/2016 | Murphy |
| 9,883,954 | B1 | 2/2018 | Murphy |
| 10,004,752 | B2 | 6/2018 | Murphy |
| 2003/0153829 | A1 | 8/2003 | Sarin et al. |
| 2004/0092944 | A1 | 5/2004 | Penenberg |
| 2004/0097952 | A1* | 5/2004 | Sarin ............ A61B 5/1127 606/91 |
| 2004/0152970 | A1* | 8/2004 | Hunter ............ A61F 2/4425 600/424 |
| 2004/0210233 | A1 | 10/2004 | Yoon et al. |
| 2004/0254586 | A1 | 12/2004 | Sarin et al. |
| 2004/0260312 | A1 | 12/2004 | Magnusson et al. |
| 2005/0076441 | A1 | 4/2005 | Dominati et al. |
| 2005/0107799 | A1 | 5/2005 | Graf et al. |
| 2005/0148843 | A1 | 7/2005 | Roose |
| 2005/0149050 | A1 | 7/2005 | Stifter et al. |
| 2005/0197569 | A1* | 9/2005 | McCombs ........ A61B 34/20 600/426 |
| 2005/0234332 | A1 | 10/2005 | Murphy |
| 2006/0025778 | A1 | 2/2006 | Ferree |
| 2006/0052795 | A1 | 3/2006 | White |
| 2006/0100504 | A1 | 5/2006 | Jansen et al. |
| 2006/0161167 | A1 | 7/2006 | Myers et al. |
| 2006/0184177 | A1 | 8/2006 | Echeverri |
| 2006/0225529 | A1 | 10/2006 | Fischer et al. |
| 2006/0241441 | A1 | 10/2006 | Chinn |
| 2007/0239169 | A1* | 10/2007 | Plaskos ............ A61B 90/39 606/96 |
| 2008/0009697 | A1* | 1/2008 | Haider ............ A61B 34/10 600/407 |
| 2008/0255584 | A1 | 10/2008 | Beverland et al. |
| 2008/0287954 | A1 | 11/2008 | Kunz et al. |
| 2009/0163922 | A1 | 6/2009 | Meridew et al. |
| 2009/0171370 | A1 | 7/2009 | Yoon et al. |
| 2009/0254093 | A1 | 10/2009 | White et al. |
| 2009/0306679 | A1 | 12/2009 | Murphy |
| 2011/0196433 | A1 | 8/2011 | Kleiner |
| 2012/0245647 | A1 | 9/2012 | Kunz |
| 2013/0006255 | A1 | 1/2013 | Murphy |
| 2013/0018430 | A1 | 1/2013 | Murphy |
| 2015/0289891 | A1 | 10/2015 | Murphy |
| 2017/0035580 | A1 | 2/2017 | Murphy |

FOREIGN PATENT DOCUMENTS

| | | |
|---|---|---|
| JP | 2004-89653 A | 3/2004 |
| JP | 2005-111257 A | 4/2005 |
| JP | 2006-501972 A | 1/2006 |
| JP | 2011-502626 A | 1/2011 |
| SU | 441 933 | 9/1974 |
| WO | WO 00/30557 | 6/2000 |
| WO | WO 01/34017 | 5/2001 |
| WO | WO 03/009768 | 2/2003 |
| WO | WO/2004/021898 | 3/2004 |
| WO | WO/2005/046451 | 5/2005 |
| WO | WO-2006/109983 A1 | 10/2006 |
| WO | WO-2008/145287 A1 | 12/2008 |

OTHER PUBLICATIONS

English Description of Japanese Publication No. JP2004-089,653, retrieved on Aug. 27, 2014, pp. 1-30.

English Description of Japanese Publication No. JP 2005-111,257, retrieved on Aug. 27, 2014, pp. 1-26.

English Translation of Office Action, from Japanese Patent Office for Japanese Patent Application No. JP 2013-112536, dated Apr. 1, 2014, pp. 1-2.

European Search Report, European Application No. 13153236.8-1659 / 2626031, Applicant: Stephen B. Murphy, dated Aug. 22, 2014, pp. 1-5.

Notification of Transmittal of the International Search Report and the Written Opinion of the International Searching Authority, or the Declaration, International Filing Date: Oct. 30, 2008, International Application No. PCT/US2008/012300, Applicant: Stephen B. Murphy, dated Mar. 5, 2009, pp. 1-8.

Archibald, H. A. P., et al., "The Transverse Acetabular Ligament: An Aid to Orientation of the Acetabular Component During Primary Total Hip Replacement: A Preliminary Study of 1000 Cases Investigating Postoperative Stability, " British Editorial Society of Bone and Joint Surgery, Journal Bone Joint Surgery, vol. 88-B, No. 7, Jul. 2006, pp. 883-886.

Chow, JC, et al., "Evaluation of Intraoperative Pelvic Positioning Using Software-based Computed Tomography/Radiography Matching," International Society for Computer Assisted Orthopedic Surgery, Jun. 2008, pp. 192-194.

Klingenstein, G., et al., "Pelvic Tilt Before and After Total Hip Arthroplasty," International Society for Computer Assisted Orthopedic Surgery, Jun. 2008, pp. 99-100.

Chen, Bin, et al., "Personalized Image-Based Templates for Precise Acetabular Prosthesis Placement in Total Hip Arthroplasty: A Pilot Study," Journal of Zhejiang University—SCIENCE B (Biomedicine & Biotechnology), Sep. 11, 2010, pp. 673-680.

Murphy, Stephen, et al., "Evaluation of Intraoperative Pelvic Position During Hip Arthroplasty Using Computed Tomography/ Radiography Matching," Oral Session 18, The 21$^{st}$ Annual Congress of the International Society for Technology in Arthroplasty, Seoul Korea, Oct. 1-4, 2008, one page.

(56) References Cited

OTHER PUBLICATIONS

U.S. Appl. No. 15/887,604, filed Feb. 2, 2018 by Stephen B. Murphy, M.D. for an Acetabular Template Component and Method of Using Same During Hip Arthrosplasty, pp. 1-31.

* cited by examiner

US 11,992,271 B2

SURGICAL SYSTEM USING A REGISTRATION DEVICE

CROSS-REFERENCE TO RELATED APPLICATIONS

The present application is a continuation of U.S. patent application Ser. No. 13/764,637, filed Feb. 11, 2013, by Stephen B. Murphy for Surgical System Using a Registration Device, which claims priority to U.S. Provisional Patent Application Ser. No. 61/597,289, filed Feb. 10, 2012, by Stephen B. Murphy and William S. Murphy for a Robotic Surgical System, and is a continuation-in-part of U.S. patent application Ser. No. 13/537,654, filed Jun. 29, 2012, by Stephen B. Murphy for a Method and Apparatus for Determining Acetabular Component Position, now U.S. Pat. No. 9,101,378, which application is a divisional of U.S. patent application Ser. No. 12/134,545, filed Jun. 6, 2008, by Stephen B. Murphy for a Method and Apparatus for Determining Acetabular Component Positioning, now U.S. Pat. No. 8,267,938, which claims priority to U.S. Provisional Patent Application Ser. No. 60/984,425, filed Nov. 1, 2007, by Stephen B. Murphy for a Method for Determining Acetabular is Component Positioning, which applications are hereby incorporated by reference in their entireties.

SUMMARY OF THE INVENTION

Briefly, the present invention relates to systems and methods for creating one or more patient-specific surgical plans, and utilizing those plans during a surgical procedure. The present invention also relates to surgical instruments, including instruments for registering at least a portion of a patient during a surgical procedure, and methods for using such registration instrument. The surgical plans may be based on a computer-generated model representing a portion of the patient's anatomy, such as the patient's pelvis in the case of hip replacement surgery. The model may be created from one or images taken of the patient. The plans may incorporate the use of one or more surgical instruments, including a registration instrument. The plans may be provided to a surgeon. The surgeon may use the registration instrument to register the portion of the patient's anatomy that is to be operated on as set forth in the plans. A digitizing probe and a tracking system may be used to capture spatial location data for a plurality of points on the instrument and on the patient's anatomy. Alternatively, a tracker may be attached to the instrument for use in tracking its location. A patient-based coordinate system may be established using the registration instrument, the captured spatial location data or a combination of the registration instrument and the captured spatial location data. The coordinate system may be used to attach one or more prosthetic components to the patient at locations and/or orientations specified in the plans. The tracking system may track the position of one or more surgical tools during the procedure, for example to assist in the placement of the prosthetic components. A control system may robotically control the one or more surgical tools during the procedure.

BRIEF DESCRIPTION OF THE DRAWINGS

The invention description below refers to the accompanying drawings, of which.

DETAILED DESCRIPTION OF AN ILLUSTRATIVE EMBODIMENT

Pre-operative Procedures

Obtain Image or Other Data

Figure 1:
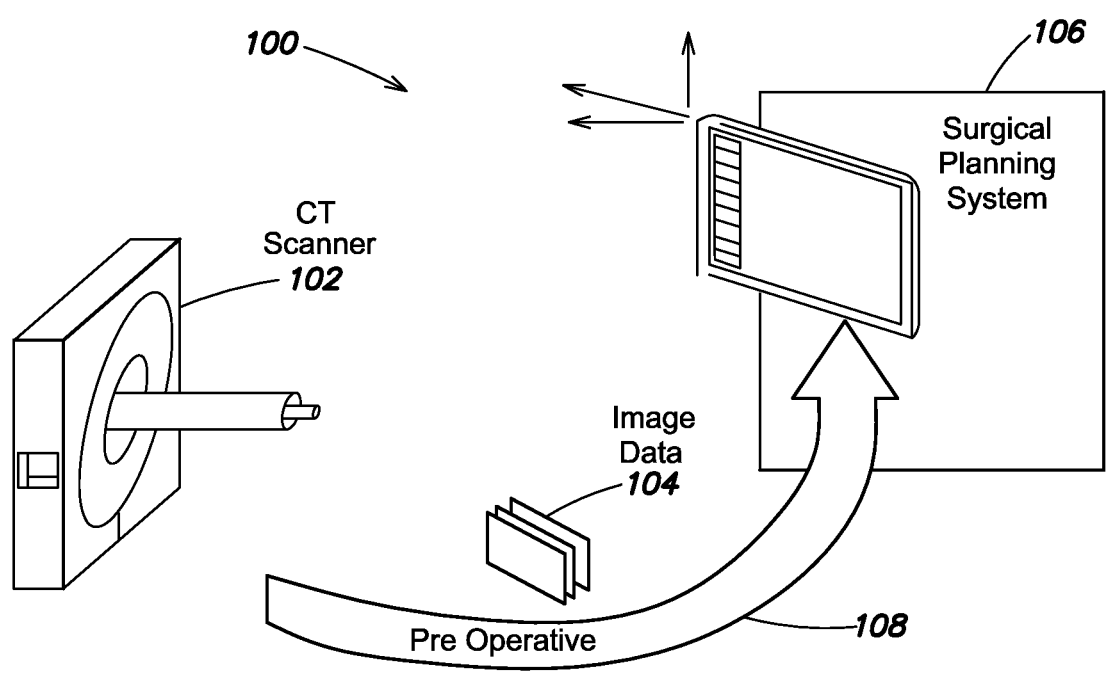
FIG. 1 is a schematic illustration of a system for capturing patient specific image is data in accordance with an embodiment of the present invention.
Figure 3A:
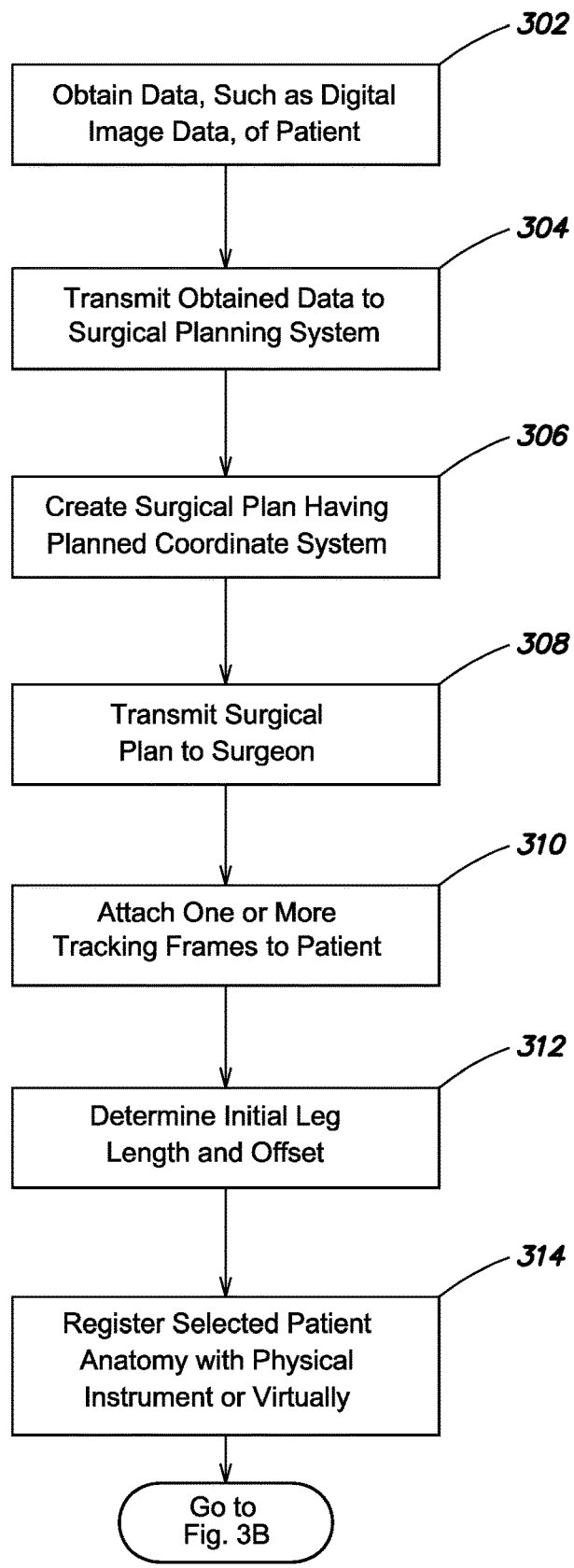
FIGS. 3A-3B is a flow diagram of a method in accordance with an embodiment of the present invention.
Figure 3B:
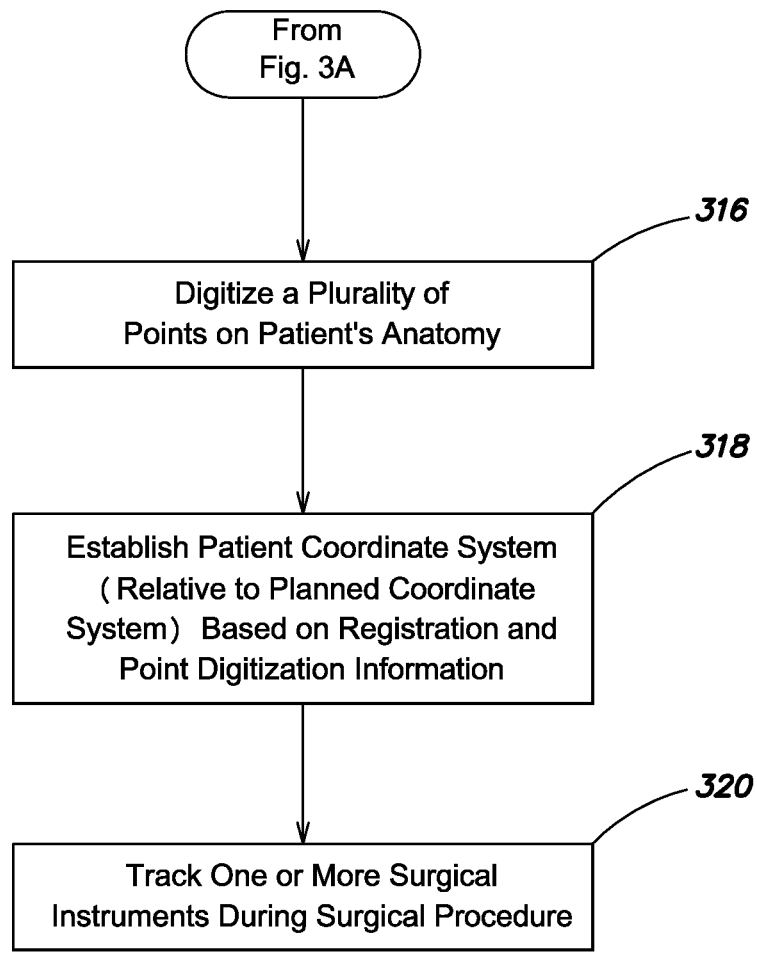

A patient may be diagnosed with a medical condition that requires surgery. In preparation for the surgical procedure, one or more data gathering procedures may be performed. FIG. 1 is a schematic illustration of a data capture system 100. The system 100 may include an imaging apparatus 102, such as Computed Tomography (CT) scanner, for generating patient-specific, pre-operative data 104, such as image data. The image data may be in the form of files or objects. The data capture system 100 may further include or be in communication with a surgical planning system 106. FIGS. 3A-B is a flow diagram of a method in accordance with an embodiment of the present invention. Specifically, data, such as the image data 104, may obtained for a patient who is to undergo a surgical procedure, as indicated at block 302. The image data 104 may be obtained of that portion of the patient's anatomy on which the surgery is to be performed. For example, a patient may be diagnosed with hip joint failure, and may require total hip replacement (THR) surgery. In this case, one or more low cost, low dose CT scans of the patient's hip may be taken. The obtained data may be transferred to the surgical planning system, as indicated at block 304, and by arrow 108 (FIG. 1).

It should be understood that patient-specific data may be obtained in other ways besides or in addition to CT scans. For example, one or more of Magnetic Resonance Imaging (MRI), conventional radiographs (X-rays), bi-planar or multiplanar simultaneous radiographs, or ultrasonic images, may be taken of the patient. The one or more digital images (CT, magnetic, radiographic, ultrasonic, etc.) may provide three-dimensional (3D) information regarding the surface and/or structure of the patient's hip.

The 3D information may be generated in other ways. For example, the 3D surface and/or structure of a patient's hip may be predicted or derived from a single image, a statistical model, one or more measurements taken of the patient's hip, etc.

Create Surgical Plan

Next, a surgical planner, such as an experienced surgeon or other person, may create a surgical plan that may be specific to the patient, as indicated at block 306. The surgical plan may specify locations and/or orientations of one or more prosthetic components to be attached to the patient. For example, the surgical plan may specify a is desired position and orientation of a prosthetic cup component at a patient's acetabulum. It may also specify a desired position and orientation of a prosthetic stem component at the patient's femur. Additionally or alternatively, the surgical plan may specify a particular volume or portion of bone or other material that is to be removed during the surgical procedure. For example, the surgical plan may specify a particular volume or portion of bone in and/or around the patient's acetabulum that is to be removed, e.g., reamed, in order to receive the acetabular cup component. Additionally or alternatively, the surgical plan may specify a value or a limit for one or more pre and post operative conditions, such as a limit for acceptable leg length and offset changes, and values for flexion, abduction, femoral anteversion, and/or combined anteversion.

The surgical planner may obtain the one or more digital images, and utilize them to create a surgical plan for the procedure. The surgical planner may utilize a 3D modeling tool to create a computer-generated, 3D model of the patient's anatomy, such as the patient's hip or portion thereof, based on the one more obtained digital images. Using the 3D model (or a statistically based 3D model), both a standard pelvic coordinate system, such as the anterior pelvic (AP) plane coordinate system, and a patient-specific ipsilateral hemipelvic plane coordinate system may be defined in the surgical plan. For example, a first set of three points on the 3D model of the patient's pelvis may be selected to define the AP plane coordinate system or another standardized reference coordinate system. A second set of three (or more) predetermined points on the 3D model of the patient's pelvis may also be selected in order to establish another plane, such as an ipsilateral hemipelvic plane and coordinate system. The plan, moreover, may incorporate or provide a translation between the AP plane coordinate system and the ipsilateral hemipelvic plane coordinate system.

A suitable registration instrument and its use are described in U.S. Pat. No. 8,267,938. This particular instrument may be referred to herein as a HipSextant instrument.

In an embodiment, the registration instrument may be adjustable, and the surgical planner may calculate one or more inputs and/or adjustments to be made on the one or more registration instruments for use with the patient. The inputs and/or adjustments is may be based, at least in part, on the 3D model of the pelvis that was created, on some or all of the patient-specific information, and/or on statistical information known to or accessible by the surgical planner. For example, the inputs and/or adjustments may be used in order to make a direction indicator, such as a guide, of the HipSextant instrument point in a direction of a desired orientation for the acetabular cup component. Furthermore, knowledge of supine and/or standing pelvic tilt, which may be provided as part of the patient-specific information, can be incorporated in the adjustments to be made to the registration instrument.

The surgical plan may thus include a series of inputs or adjustments to be made to one or more registration instruments before or during the procedure. The surgical plan may further include instructions for setting up and using the one or more registration instruments during the procedure. In other embodiments, the surgical plan may be or may include machine instructions, such as executable code, for controlling or operating one or more machines, such as a robotically controlled surgical tool or other machine to perform or assist during the surgical procedure. The surgical plan may further include machine instructions to be executed by the robotic surgical tool that will perform all or part of the procedure. For example, the surgeon may register a body part of the patient in accordance with one or more requirements, and once the body part is registered, an active, semi-active, or haptic robot may be used to perform all or part of the surgical procedure according to instructions in the surgical plan or a locally updated surgical plan according to input by the surgeon. The robot, moreover, may be computer-controlled in the operating room. In addition to controlling a surgical robot, the surgical plan may provide instructions for controlling a free-hand surgical device, such as a rotating tool, to turn on when it is in a location where cutting, drilling or other operations are to be performed and either turn off or deploy a protective sheath when the device is in a location where cutting, drilling or other operations should not take place.

Exemplary surgical robots include the surgeon-controlled robotic arms from Mako Surgical Corp. of Fort Lauderdale, Fla. Exemplary free-hand tools include the freehand sculptor from Blue Belt Technologies, Inc. of Pittsburgh, Pa.

In an embodiment, the surgical plan may include one or more 3D printer files that is may be used to operate a locally controlled 3D printer to create a single-use, patient-specific instrument or prosthetic component, such as a component designed to mate with the patient's anatomy, such as the patient's hip, knee or other joint. For example, the component may fit uniquely onto patient-specific anatomy in or adjacent to a joint of the patient, and provide the specific orientation and location of a drill guide to be used during the surgical procedure on the patient. The surgeon or a technician may utilize the one or more 3D printer files to run the 3D printer and construct the patient-specific component. The 3D printer may be located at the hospital at which the surgery is to be performed or it may be located at another facility, such as a quality-controlled manufacturing facility that is local to the hospital.

A suitable component or template is described in U.S. Pat. No. 8,986,309 for an ACETABLULAR TEMPLATE COMPONENT AND METHOD OF USING SAME DURING HIP ARTHROPLASTY by Stephen Murphy, which is hereby incorporated by reference in its entirety.

Once completed, the one or more electronic surgical plans created by the surgical planner may be transmitted to the surgeon performing the procedure, as indicated at block 308. For example, the one or more plans may be transmitted by facsimile, electronic mail (email), text messaging, and/or made available on a website for downloading. The one or more plans also may be fetched automatically from a server, e.g., using a locally operating application on a local data processing machine or device, such as a desktop computer, a laptop computer, a tablet computer, a smart mobile phone, etc.

It should be understood that the plan may be generated locally to where the procedure is being performed, e.g., at a hospital or other medical facility. Furthermore, the plan may be created by the surgeon who will be performing the procedure.

Surgical Procedure

Figure 2:
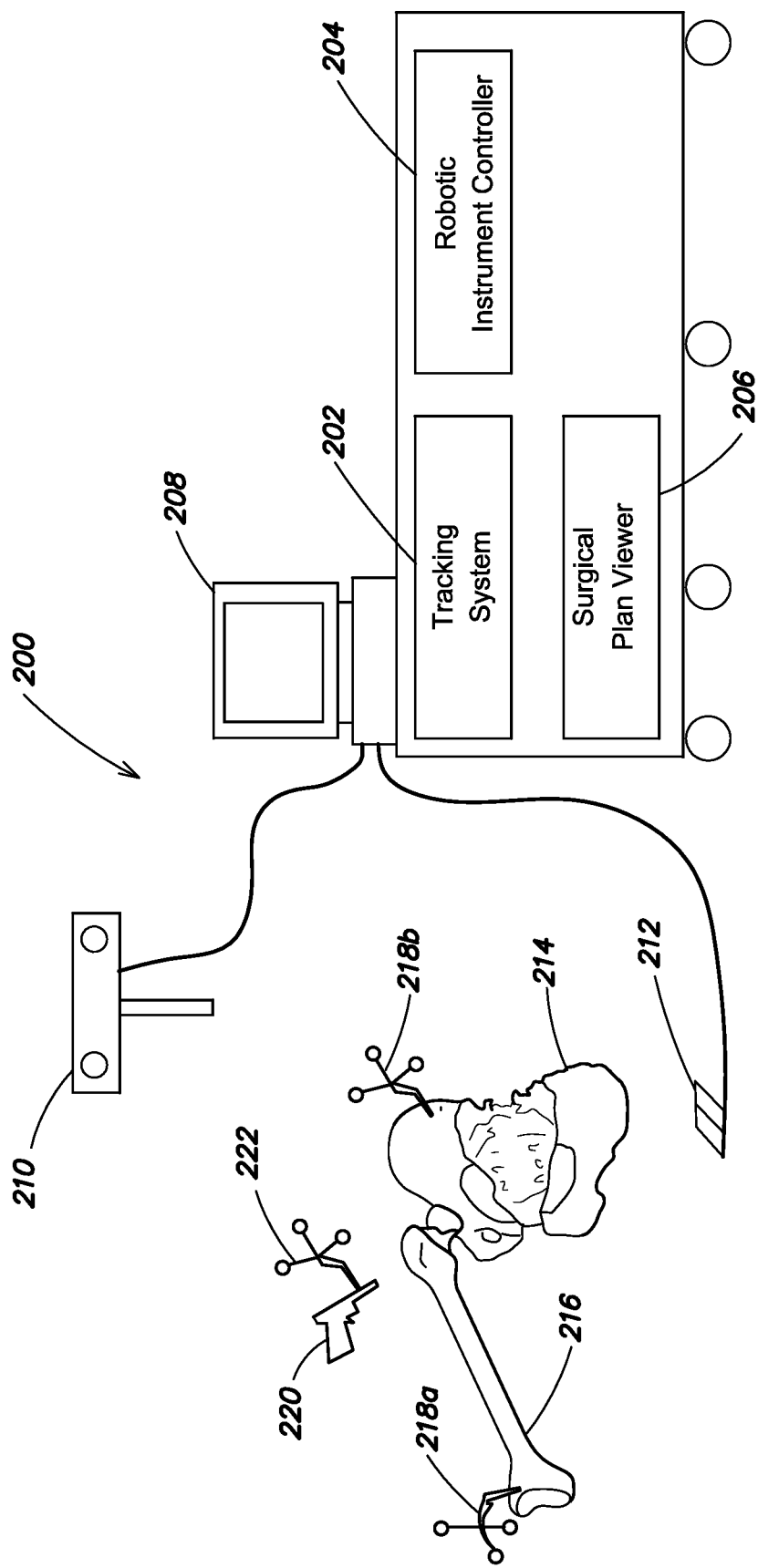
FIG. 2 is a schematic illustration of an operating room in accordance with an embodiment of the present invention.

FIG. 2 is a schematic, partial illustration of an operating room 200. Disposed in the operating room 200 may be a tracking system 202, a surgical plan viewer 204 and a robotic instrument controller 206. One or more of the tracking system 202, the surgical plan viewer 204 and the robotic instrument controller 206 may be implemented as software modules on a data processing device 208, such as a computer. A tracking unit 210 and a controller 212, such as a foot control, may be coupled to the computer 208.

Also disposed in the operating room may be the patient being operating on, as illustrated by pelvis 214 and femur 216. One or more tracking frames 218a and 218b, or trackers, may be attached to the patient, as part of the surgical procedure being performed on the patient, as indicated at block 310. For example, at least one tracker 218b may be attached to the patient's pelvis 214, and at least one tracker 218a may be attached to the patient's femur 216.

Suitable trackers and tracking systems include infrared optical trackers and tracking systems, such as the Stealth Station S7 family of surgical navigation systems from Medtronic. Other suitable tracking technology and systems include electromagnetic (EM) trackers and tracking systems, such as the driveBAY trackers and system from Ascension Technology Corp., ultrasound, inertial navigation, acoustic, and video. In another embodiment, no trackers may be attached to the patient, or one or more trackers may be attached just to the patient's pelvis or another portion of the patient.

The surgeon may determine one or more initial (pre-operative) patient measurements, such as leg length and/or offset, as indicated at block 312. A suitable technique for measuring these values, and for performing a trial reduction of an artificial hip is described in U.S. Pat. No. 7,885,705, issued Feb. 8, 2011, for a SYSTEM AND METHOD FOR FACILITATING HIP SURGERY, which is hereby incorporated by reference in its entirety.

It should be understood that the method may include fewer, greater or other steps. For example, attached one or more trackers to the patient as described at step 310 and/or determining leg length and/or offset as described at step 312 may be option and may not be performed.

Registration of the Pelvis.

If the surgical plan incorporated a surgical instrument, such as a mechanical registration instrument like the Hip-Sextant instrument, then the instrument may be adjusted for the patient as pre-operatively determined during the planning stage. In an embodiment, the legs of the instrument may be adjustable relative to each other. For example, the legs of the registration instrument may be adjusted relative to each other, as pre-operatively determined for the specific patient. Two of the legs of the registration instrument may be mounted to adjustable arms, and the arms may be adjusted, e.g., extended or retracted, to predetermined values. Markings along the arms may be used to set the legs to the specified lengths. Alternatively, the legs may be mounted to a central hub and be angularly adjusted relative to each other in the manner of a camera tripod. In yet another embodiment, prior to the surgical procedure, a non-adjustable, patient-specific registration instrument may be manufactured having the pre-operatively determined distances between the tips of the legs. Such an instrument may be discarded following the procedure.

Once the registration instrument has been adjusted in accordance with the pre-operative plan, the registration instrument may be docked, e.g., attached, to the patient according to the plan, thereby registering the patient or more specifically the patient's pelvis 214, as indicated at block 314. For example, the plan may specify the points, e.g., three points, at which the tips of the legs of the registration instrument are to be docked to the patient's pelvis 214 in order to establish a patient-based 3D coordinate system, such as an ipsilateral hemipelvic coordinate system. In particular, the HipSextant instrument, based on its physical construction (as adjusted), may establish an ipsilateral hemipelvic coordinate system including a hemipelvic plane, when docked to the patient.

With the instrument docked or attached to the patient, one or more, and preferably three or more (non-collinear), points on the instrument may be digitized using a navigation pointer, also referred to as a digitizing probe, as indicated at block 316 (FIG. 3B). A navigation pointer is a device typically having a tip and a tracker, such as an optical tracker, having a known spatial relationship relative to the tip. The tip of the pointer may be placed on specific points of the registration instrument, and the spatial position of the tip, which represents a point, may be captured by the tracking system. The registration instrument may include mechanical or other features, such as divots, at three or more locations on the instrument for receiving the tip of the pointer. For example, the divots may be located on the frame and/or arms of the instrument. The divots may be located at points that define a plane that is parallel to the ipsilateral hemipelvic plane defined by the tips of the legs of the instrument when it is docket to the patient. The tracking system 202 may determine the 3D spatial coordinates of these points relative to a coordinate system defined by the tracking system. In the this way, the orientation, for example the angular orientation, of the patient's hip may be registered, for example relative to the coordinate system defined by the tracking system 202.

Figure 9:
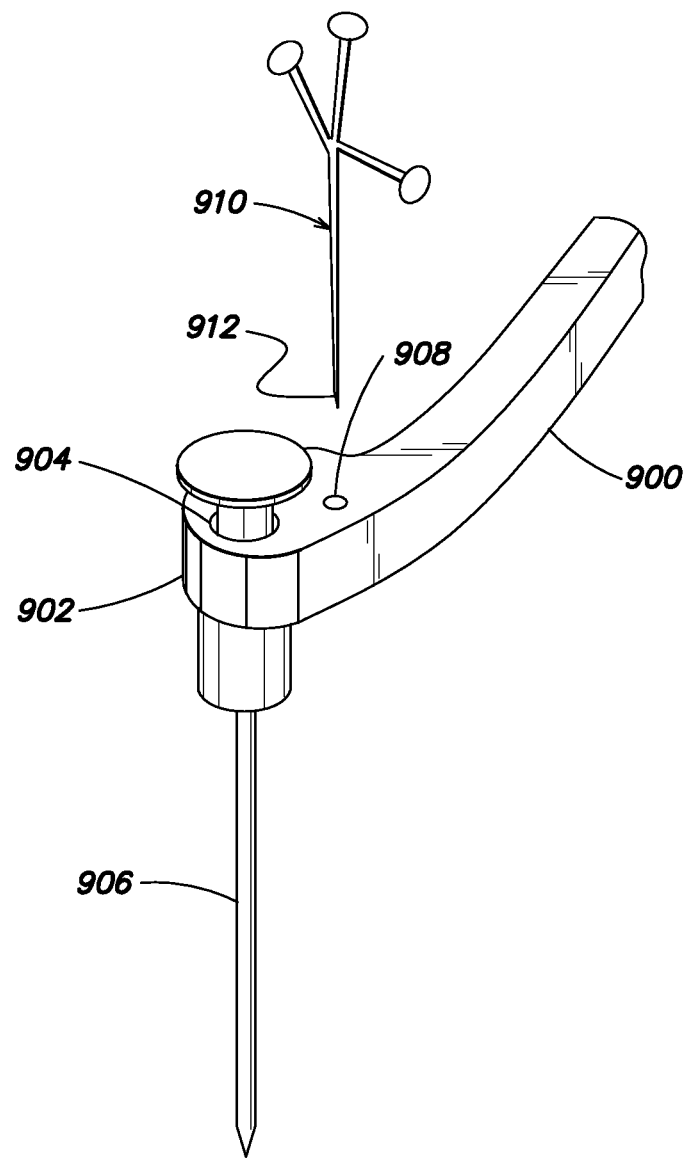
FIG. 9 is a perspective, partial view of an arm of a registration instrument in accordance with an embodiment of the present invention.

FIG. 9 is a perspective, partial view of an arm 900 of a registration instrument. The arm 900 may have a terminal portion 902 that includes a hole or slot 904 for receiving one of the legs of the instrument, such as the first or basepoint leg 906. The basepoint leg 906 may be secured within the slot 904 of the arm 900 by a clamp or locking screw (not shown), e.g., a basepoint clamp. Formed in the surface of the arm 900 may be at least one divot 908. A digitizer 910 having a tip 912 may be moved toward the registration instrument, and the tip 912 of the digitizer 910 may be placed in the divot 908 on the arm 900 of the registration instrument. With the tip 912 in the divot 908, the tracking system 202 may capture the location of the tip 912 of the digitizer 910, thus capturing a point on the arm 900 registration instrument defined by the location of the divot 908. A second divot may be formed on the other arm (not shown) of the instrument, and a third divot may be formed on the central hub portion of the instrument from which the two arms extend. By digitizing these three points, the ipsilateral hemipelvic plane and coordinate system established by the registration instrument may be captured by the tracking system 202.

In another embodiment, one or more trackers may be attached to the registration instrument. The one or more trackers may be fixedly or removably attached to the registration instrument. For example, a tracker may be permanently mounted to the registration instrument, or a saddle or receptacle may be incorporated into the registration instrument, and a tracker may be removably attached to this saddle or receptacle. Once attached or seated to the registration instrument, the tracking system 202 may capture and "memorize" the location of the registration instrument and its D3 coordinate system relative to one or more other trackers attached to the patient, e.g., to the patient's pelvis. In this way, the ipsilateral hemipelvic plane and coordinate system may be established relative to the one or more trackers on the patient's pelvis and/or to the AP plane and coordinate system.

Using this information, the pelvis may be registered relative to the at least one tracker, because the location of the tracker relative to the ipsilateral hemipelvic plane coordinate system can be determined. Furthermore, because the surgical plan may include a translation function between the ipsilateral hemipelvic plane coordinate system and the AP plane coordinate system, the relationship between the tracker and the AP plane coordinate system can also be determined. With the ipsilateral hemipelvic plane coordinate system captured by the tracking system 202, the registration instrument may be removed from the patient.

To provide additional navigation data, for example to more accurately establish the patient-based coordinate system, a plurality of points on the patient's anatomy may also be digitized, i.e., captured by the tracking system 202. For example, for hip arthroplasty, a plurality of points at and around the patient's acetabulum may be digitized, using the pointer. That is, upon accessing the patient's acetabulum, the surgeon may digitize a plurality of points inside and/or around the acetabulum. These points may be combined with hemipelvic plane defined by the registration instrument, when docked to the patient, to establish a coordinate system, as indicated at block 318. More specifically, the tracking system 202 may be configured to compute a center of rotation for the acetabulum based on the plurality of points. The tracking system 202 may set this center of rotation as the origin of the coordinate system. In an embodiment, the surgeon may digitize a large number of points in close proximity to each other to establish the origin. In this embodiment, the registration instrument may be used primarily to establish the axes of the coordinate system, such as x, y and z axes. That is, the registration instrument in combination with a plurality of points on the patient's anatomy, such as in the acetabulum, may be used to establish a coordinate system that includes the ipsilateral hemipelvic plane.

In some cases, a patient's preoperative anatomy may be such that an origin may not be capable of being determined. For example, a patient's acetabulum may be distorted such that a center of rotation cannot be determined. In this case, a cloud of points, for example within and/or outside of the acetabulum, maybe digitized, and a "best fit" matching computation performed, such as a root mean square minimization calculation, that determines how the cloud of captured points may best fit the 3D model surface.

It should be understood that depending on the procedure being performed other points on the patient's anatomy may be digitized. Furthermore, points, such as a cloud of points on a bone surface, may be captured by or entered into the tracking system 202 using a tracked ultrasound probe.

In an embodiment, once the coordinate systems are established on the patient, the registration instrument may be removed, and the surgical procedure may be continued. That is, the registration instrument may register the patient in the operating room 200, and this registration can be tracked by the tracking system 202 through the trackers 218a, 218b attached to the patient. The tracking system 202 may track one or more instruments used by the surgeon during the procedure, as indicated at block 320. For example, the tracking system 202 may track one or more instruments manually operated by the surgeon to, e.g., attach one or more prosthetic components, such as an acetabular cup, to the patient, as specified in the surgical plan.

Alternatively, the registration instrument may remain docked to the patient during the surgical procedure. In this case, the registration instrument may include a fixed or adjustable guide, such as a guide moveably attached to one or more protractors, and the guide, once set, e.g., as set forth in the one or more plans, may be used by the surgeon to attach the one or more prosthetic components at the desired locations and/or orientations. To the extent the registration instrument further includes one or more guides, it may be referred to as a registration, tracking and navigation instrument.

The registration instrument may be attached to the patient as set forth in the one or more surgical plans. In an embodiment, the tip of a first leg of the registration instrument may be positioned at a first point (referred to as the basepoint) located in the area of the posterior inferior acetabulum. The tip of the second leg may be positioned at a second point (referred to as the ASIS point) located in the area of the anterior superior iliac spine. The tip of the third leg may be positioned at a point located on the ilium, e.g., where the bone is dense. The first and second points may be readily identified by the surgeon during the procedure. The surgeon may not, however, directly identify the location of the third point. Instead, the tip of the third leg may land at the third point after the tips of the first and second legs are placed at the first and second points on the pelvis.

In an embodiment, the surgeon may use other instruments, such as one or more jigs, drill guides, patient-specific or non-patient specific templates, etc., to locate the basepoint for receiving the tip of the first leg of the registration instrument. In addition, the distance between the tip of the first leg of the instrument and the tip of the second leg of the instrument may be fixed, e.g., set to a desired distance and locked, thereby assisting the surgeon in locating the second point, given that the second point is a constrained distance from the first point. By having or setting the tip of the second leg to a prescribed distance from the tip of the first leg, any error in locating the second point may be reduced.

In another embodiment, the registration instrument may not be docked or attached to the patient at all. Instead, the points at which the HipSextant instrument would dock or attach to the patient's pelvis may be digitized using the pointer. For example, the first point on the patient's pelvis referred to as the basepoint may be digitized, using a digitizing probe that is tracked by the tracking system 202. Next, the second point, also referred to as the ASIS point, may be digitized with the digitizing probe. The ASIS point is a point on the patient's pelvis that is a fixed distance from the basepoint. The fixed distance may be determined by the person who created the surgical plan, and it may be included in the surgical plan. As the surgeon is locating the ASIS point for digitizing, the tracking system 202 may display, e.g., in real time, the distance of the probe from the basepoint to assist the surgeon in finding the ASIS point specified in the surgical plan, by helping the surgeon to keep the digitizing probe at the fixed distance from the basepoint. Next, the surgeon may digitize the point referred to as the landing point, which is a point on the ilium of the patient's pelvis. The landing point is a fixed distance from the basepoint and the ASIS point, which fixed distances may or may not be the same, as specified in the surgical plan. Again, the tracking system 202 may be adapted to track the digitizing probe as the surgeon locates the landing point. In addition, the tracking system 202 may display the digitizing probe's distance from the basepoint and from the ASIS point, e.g., in real time, to assist the surgeon in locating the landing point with the digitizing probe. Thus, the location of patient-specific ipsilateral hemipelvic plane coordinate system and the anterior pelvic plane coordinate system may be determined using a virtual HipSextant as opposed to using the actual physical instrument, as indicated at block 314 (FIG. 3A).

Basepoint Inside the Acetabulum

Figure 4:
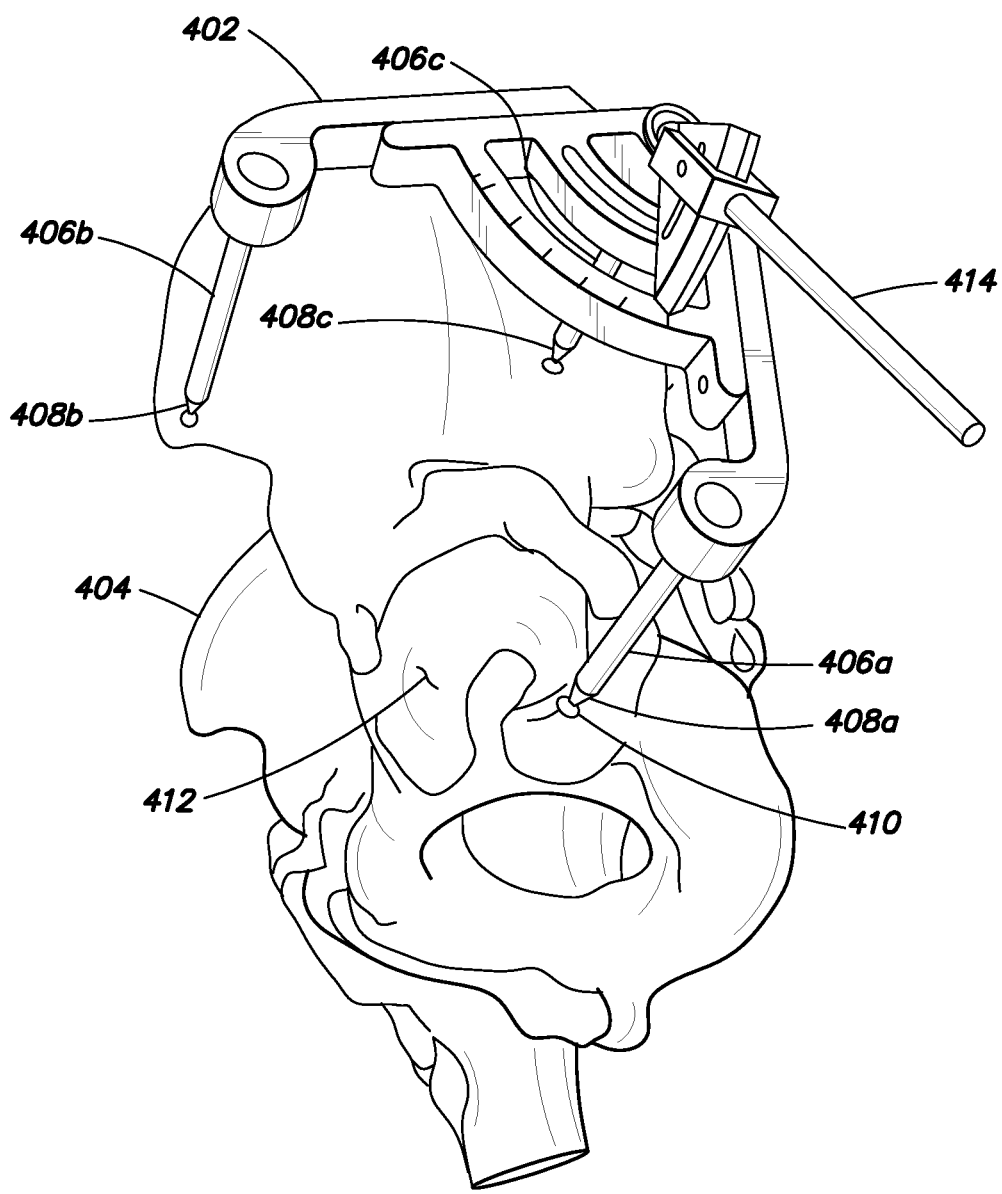
FIG. 4 is a schematic perspective view of a model of a pelvis and a registration instrument in accordance with an embodiment of the present invention.

In another embodiment, the basepoint may be located inside the acetabulum. Such an embodiment may be well suited for the anterolateral and anterior approaches of total hip replacement. More specifically, a posterior location of the acetabulum may be selected during the pre-operative planning stage for the basepoint location. The second and third points may be selected as described above. FIG. 4 is a perspective view of a model of a registration instrument 402 docked to a model of a patient's pelvis 404. The instrument 402 includes three legs 406a-c that terminate in tips 408a-c. The tip 408a of the first leg 406a is located at a posterior location 410 of an acetabulum 412. During the procedure, one or more instruments may be used by the surgeon to locate the pre-selected posterior location for the basepoint in the patient's acetabulum. With the posterior acetabulum location determined, the surgeon may place the tip 408a of the first leg 406a of the registration instrument 402 at this location. The tip 408b of the second leg 406b of the registration instrument 402 may be placed at the predetermined point located in the area of the anterior superior iliac spine. The tip 408c of the third leg 406c of the registration instrument 402 may land at the desired location on the ilium.

As mentioned, the registration instrument 402 may include a guide 414 for defining an orientation of a line relative to the ipsilateral hemipelvic plane defined by the registration instrument 402 when docked to the patient's pelvis. Since the relationship between the ipsilateral hemipelvic plane and coordinate system and the AP plane and coordinate system and is known, for example as established during the planning stage using the 3D model, the guide 414 may be used to define an orientation of a line relative to the AP plane and coordinate system, This line may define an orientation for a prosthetic acetabular cup being inserted into the patient's acetabulum. The orientation of the guide 414 may be adjustable, and the pre-operative plan may define the settings for is the guide. The surgeon may adjust the guide to the settings specified in the one or more preoperative plans.

The orientation of the guide of the registration instrument may be transferred to the pelvis. For example, the surgeon may utilize the guide to fix a component to the patient's pelvis that is aligned with the guide. For example, a pin may be inserted into the patient's pelvis that is aligned with, i.e., is parallel to, the guide. Another instrument, such as a parallel guide may be used by the surgeon to fix the component to the patient's pelvis in alignment with, e.g., in the same orientation as, the guide on the registration instrument. A suitable parallel guide is disclosed in U.S. patent application Ser. No. 13/708,132, filed Dec. 7, 2012, by Stephen B. Murphy, for a Guide for Acetabular Component Positioning, which application is hereby incorporated by reference in its entirety.

Once the component is fixed to the patient's pelvis, the registration instrument may be removed, thereby permitting access to the acetabulum, and the surgical procedure may continue. In particular, a guide rod may be attached to the pin, and the surgeon may use this guide rod to set the orientation of the acetabular cup component. Once the acetabular cup is positioned in the acetabulum as desired, i.e., as set forth in the one or more pre-operative plans, the guide rod and pin may be removed.

Figure 5:
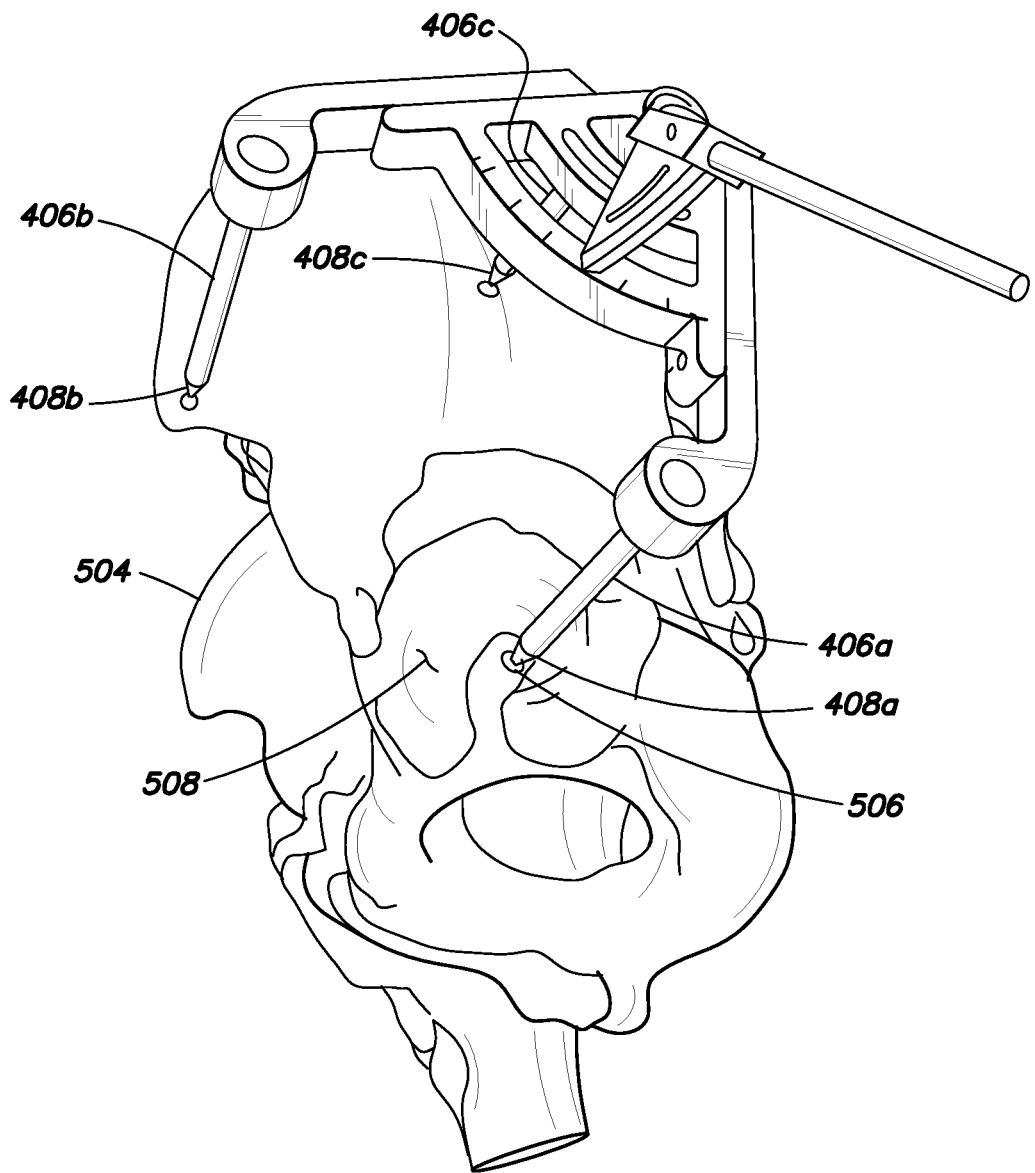
FIG. 5 is a schematic perspective view of a model of a pelvis and a registration instrument in accordance with another embodiment of the present invention.

It should be understood that other locations within the acetabulum, besides a posterior location, may be utilized as the basepoint for the registration instrument. For example, a central point on the surface of the acetabulum may be selected for the basepoint location. FIG. 5 is a perspective view of a model of the registration instrument 402 docked to a model of a patient's pelvis 504. In this embodiment, the tip 408a of the first leg 406a is located at a central location 506 of an acetabulum 508. During the procedure, one or more instruments may be used by the surgeon to locate the pre-selected posterior location for basepoint in the patient's acetabulum. With the central acetabulum location determined, the surgeon may place the tip 408a of the first leg 406a of the registration instrument 402 at this location. The tip 408b of the second leg 406b of the registration instrument 402 may be placed at the predetermined point located in the area of the anterior superior iliac spine. The tip 408c of the third leg 406c of the registration instrument 402 may land at the desired location on the ilium.

Figure 10:
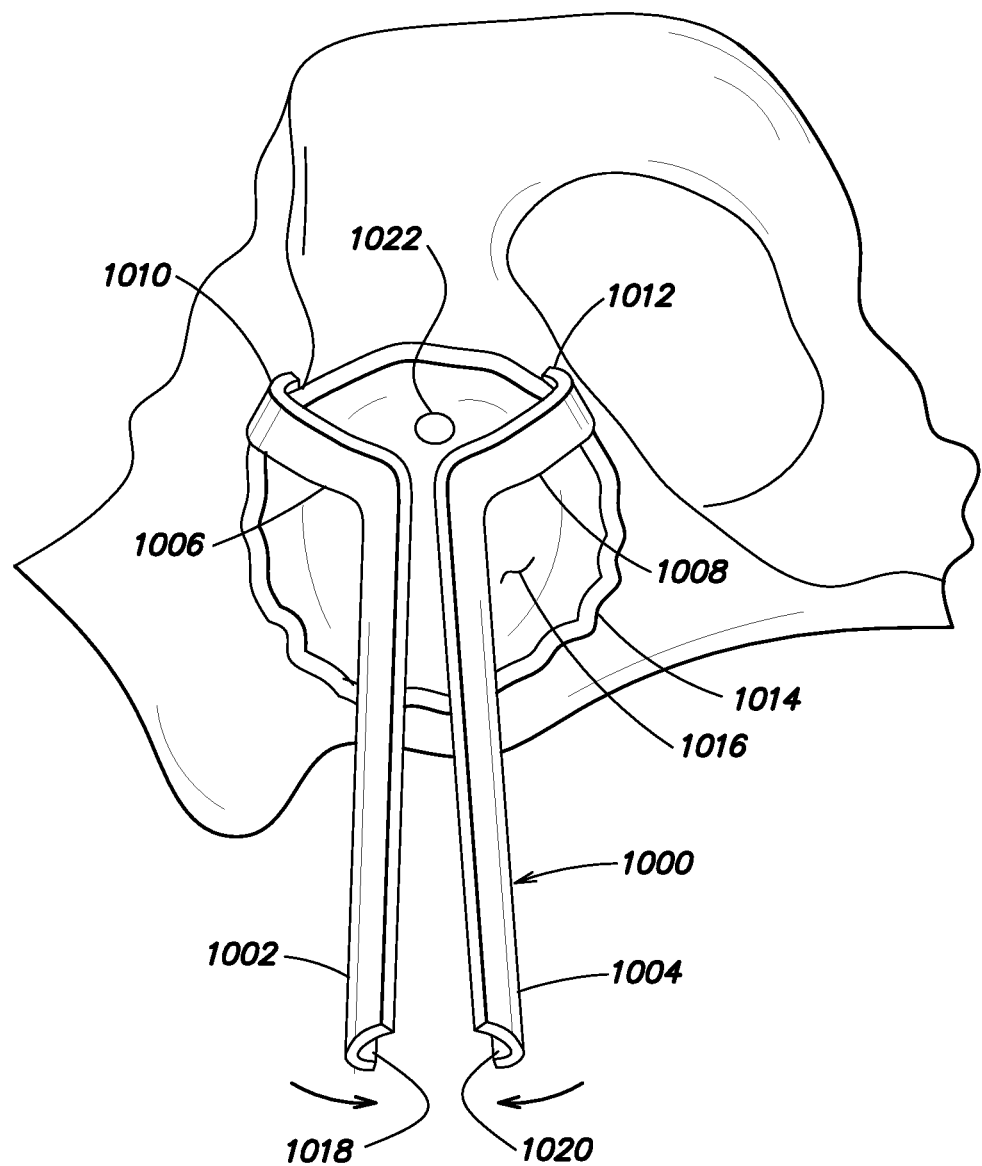
FIG. 10 is a schematic illustration of a basepoint locating instrument in accordance with an embodiment of the present invention.

As noted, one or more instruments may be used by the surgeon to help the surgeon locate the basepoint within the acetabulum. FIG. 10 is a schematic illustration of a first basepoint locating instrument 1000. The instrument 1000 may consist of two parts: a first part 1002 and a second part 1004 that each represents half or some portion of the instrument. Each part 1002, 1004 may have a hook-shaped element 1006, 1008 at a first end. The hook-shaped elements 1006, 1008 may terminate with a flange 1010, 1012 configured to hook over a rim 1014 of a patient acetabulum 1016. The first and second parts 1002, 1004 may further include a half a cylindrical slot 1018, 1020 or any shape such that when the two portions are joined together, they form a complete drill guide with two calibrated distances conferred by it.

A surgeon may hook the flanges 1010, 1012 at predetermined locations on the acetabular rim 1014. The two parts 1002, 1004 may then be brought together as illustrated by the arrows and snapped (or clamped) together to form a single instrument, such as a calibrated drill guide. A drill may be slid down the single channel formed by the two cylindrical slots 1018, 1020 when assembled together, and a hole 1022 may be drilled into the acetabulum 1016. This hole 1022 corresponds to the basepoint for the registration instrument. A pin (not shown) may be placed in the hole 1022, and the basepoint leg, which may be hollow, may be slid over the pin. In this way, the first leg of the registration instrument may be mounted to the basepoint located within the acetabulum. The tips of the second and third legs of the registration instrument may be placed and the preselected second and third points as described above.

It should be understood that the two parts 1002, 1004 including the hook-shaped elements 1006. 1008 are constructed so that, when the two parts are joined to form the instrument, the instrument identifies the location of the predetermined basepoint within the acetabulum 1016. More specifically, the instrument may be designed and constructed such that each half defines a predetermined distance from an anatomical landmark, such as a location on the acetabular rim. These two distances may be selected to intersect at one or possibly two points. The intersection of these two distances together with the surface of the pelvis define a unique point, namely the preseleted basepoint for this embodiment. It should be understood that the distances defined by the two halves of the instrument, e.g., from the rim of the patient's acetabulum, may be fixed or may be adjustable. In the case where the distances are adjustable, the one or more plans may includes values for setting these distances to predetermined values so that the instrument when used during the procedure locates the predetermined basepoint in the patient's acetabulum.

Figure 11:
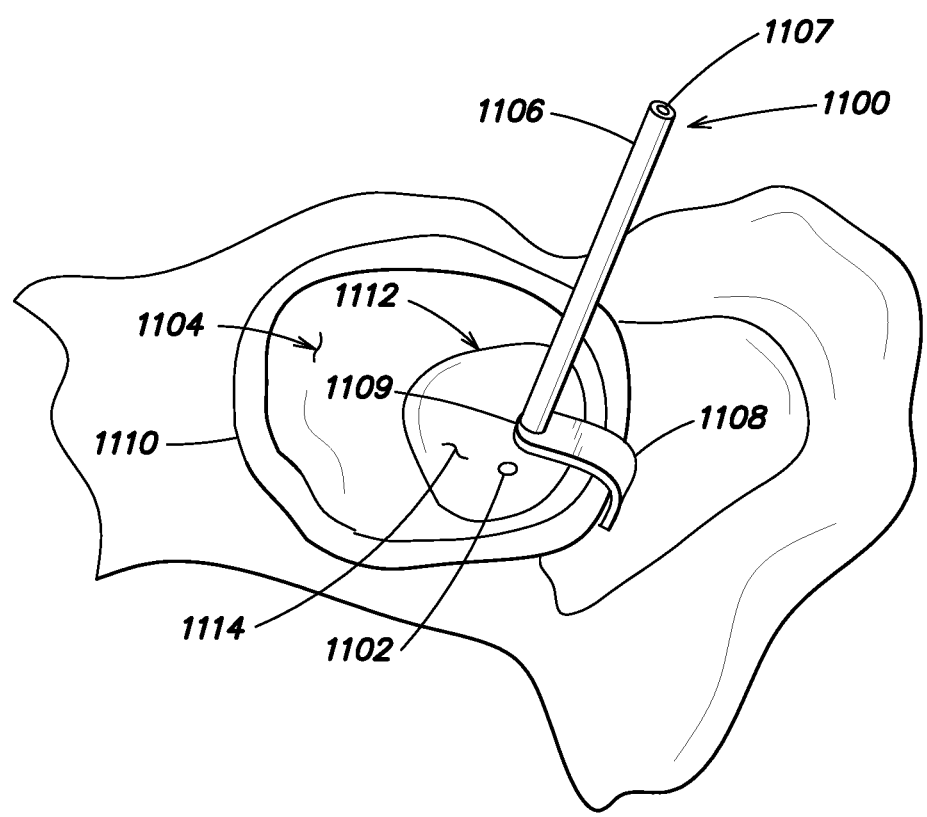
FIG. 11 is a schematic illustration of a basepoint locating system in accordance with an embodiment of the present invention.

FIG. 11 is a schematic illustration of another instrumentation system 1100 for locating the position of a predetermined basepoint 1102 within an acetabulum 1104. The instrumentation system 1100 may include a drill guide element 1106 defining an open channel 1107 extending down through a hollow arm element 1108 to a distal end 1109 of the drill guide element 1106. The arm 1108 may be configured to hook around or onto a rim 1110 of the patient's acetabulum 1104 at a particular point on the acetabular rim. The instrumentation system 1100 may also include a subsphere element 1112 that may have a rounded, e.g., convexly curved, bottom surface (not shown) for resting within the patient's acetabulum 1104. The distal end of the drill guide element 1106 may rest on an upper surface 1114 of the subsphere element 1112. With the drill guide element 1006 hooked around the rim 1110 of the patient's acetabulum 1104 and resting on the upper surface 1114 of the subsphere element 1112, the system 1100 locates the preselected basepoint 1102 (which may be underneath the subsphere element 1112). A drill (not shown) may be slide down the drill guide element 1106 to form a drill hole at the basepoint 1102. As described, a pin may be inserted into this hole, and the basepoint leg of the registration instrument may be removably placed onto this pin. The tips of the second and third legs of the registration instrument may be placed and the preselected second and third points as described above.

Figure 12:
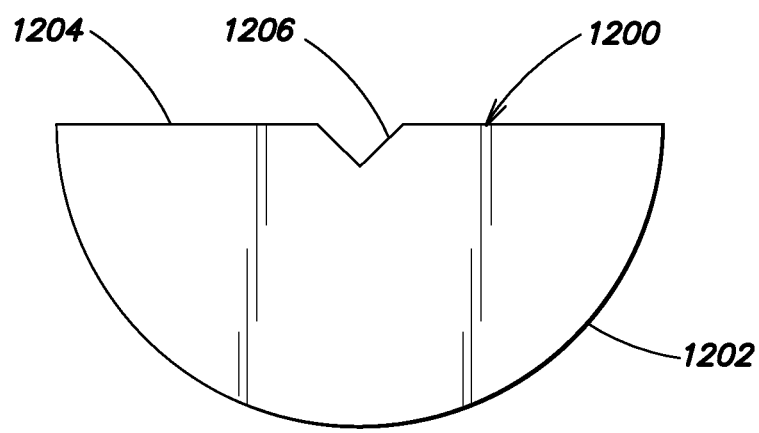
FIG. 12 is a side elevation of a basepoint locating jig in accordance with an embodiment of the present invention.

FIG. 12 is a side view of a jig 1200 for use by a surgeon in locating a basepoint that corresponds to a center of rotation of the hip. The jig 1200 may have a generally semi-spherical shape. Specifically, the jig 1200 may have a rounded lower surface 1202 shaped to fit within a patient's acetabulum (not shown). The jig 1200 may further include an upper surface 1204 in which a central notch 1206 is formed. The notch 1206 may be formed at the center of the sphere defined by the semi-spherical jig 1200. The jig 1200 may be placed in the patient's acetabulum, and the tip of the basepoint leg of the registration instrument may be placed in the central notch 1206 of the jig 1200. The tips of the second and third legs of the registration instrument may be placed and the preselected second and third points as described above. With the registration instrument thus docked or attached to the patient, the registration instrument establishes the ipsilateral hemipelvic coordinate system and therefore also the anterior pelvic plane coordinate system or any other coordinate system whose relationship is known. The registration instrument may be digitized using a digitizing probe, and the ipsilateral hemipelvic coordinate system may be captured by the tracking system 202. The registration instrument and the jig 1200 may be removed from the patient and the procedure may be continued.

As illustrated in FIGS. 4 and 5, the registration instrument may be configured so that the arm from which the basepoint leg 406a extends may be directly over the acetabulum 412, 508, and the basepoint leg 406a may be formed from a single, straight leg. It should be understood that the registration instrument may take other configurations, and still utilize a basepoint within the acetabulum.

Figure 13:
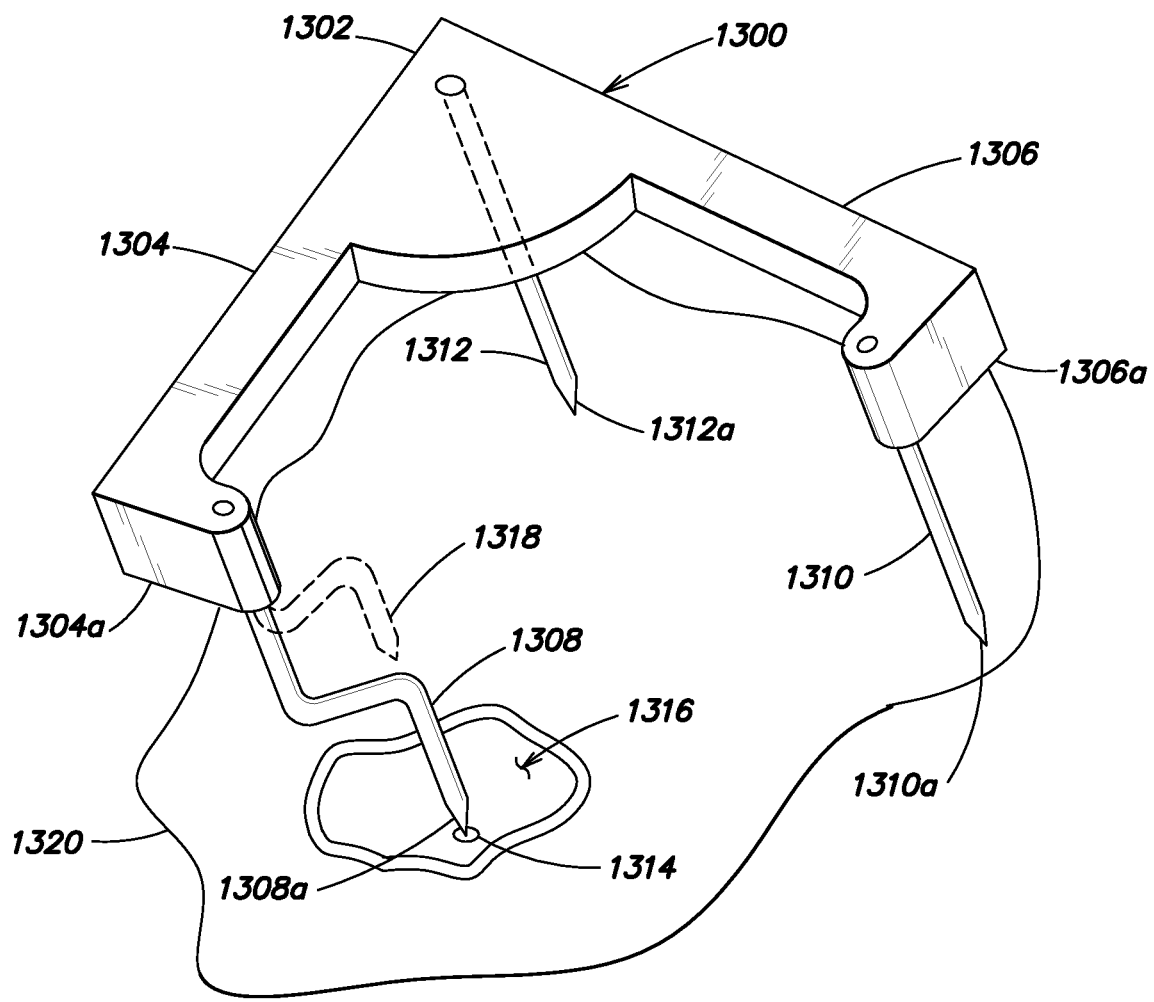
FIG. 13 is a schematic, perspective view of a registration instrument in accordance with another embodiment of the present invention.

FIG. 13 is a perspective, schematic illustration of a registration instrument 1300. The registration instrument 1300 may have a central hub portion 1302 and first and second arms 1304, 1306 that extend from the central hub portion 1302. Extending from a terminal portion 1304a of the first arm 1304 may be a first leg 1308. Extending from a terminal portion 1306a of the second arm 1306 may be a second leg 1310. A third leg 1312 may extend from the central hub portion 1302. Rather than being straight, the first leg 1308 may have one or more bends and may thus have a zigzag or offset shape so that a tip 1308a of the first leg 1308 contacts a preselected basepoint 1314 within a patient's acetabulum 1316, while the terminal portion 1304a of the first arm 1304 is not located directly above the acetabulum 1316. The first leg 1308 maybe removably attached to the first arm 1304 or it may be fixedly attached thereto. If the first leg 1308 is removably attached, it may be configured to attach to the first arm 1304 in a unique way having a fixed rotation.

The tip 1308a of the first leg 1308 may be placed at the preselected basepoint 1314 within the acetabulum 1316. Tips 1310a and 1312a of the second and third legs 1310, 1312 may be placed at the second and third points as described herein.

The registration instrument 1300 may further include an orientation guide (not shown) that may be adjustable. The orientation guide may be set as specified in the one or more plans, and a pin may be removably fixed to the patient's pelvis to record the setting of the orientation guide. This setting may thereafter be used by the surgeon to place an acetabular cup component into the patient's acetabulum 1316 at the desired orientation.

Before removing the first leg 1308, a support leg 1318 (shown in phantom) may be used to hold the registration instrument 1300 in place relative to the patient's pelvis 1320. The support leg 1318 may extend from the first arm 1304 and contact the surface of the patient's pelvis at any suitable location, e.g., a location that is out of the way of the procedure, and that provides sufficient support for the instrument 1300. The first leg 1308 may then be removed and the surgical procedure may be continued with the registration instrument 1300 remaining in place to assist the surgeon in placing a component, such as an acetabular cup component in a desired location, as set out in the one or more plans.

Instead of transferring the orientation of the guide to the patient's pelvis, the entire coordinate system including the ipsilateral hemipelvic plane coordinate system as established by the registration instrument, when docked to the patient, may be transferred from the registration instrument to the patient's pelvis. For example, the registration instrument may be used to fix a physical coordinate defining component to the patient's pelvis. The coordinate defining component may include an adjustable planar element. The adjustable planar element may be positioned parallel to the hemipelvic plane as established by the registration instrument, and locked in this position. The coordinate defining component may further include a guide element for establishing an orientation of a line. The guide element of the coordinate defining component may be aligned to the guide of the registration instrument.

Registration Instrument Having Unequal Leg Lengths

It should be understood that other registration instruments may be used. For example, while the registration instrument 402 described above has three equal length legs 406a-c, a registration instrument may have one or more legs of different, e.g., shorter length. Such a registration instrument may be suited to performing a total hip replacement procedure using the anterolateral and anterior approaches, e.g., due to an improved approach of the legs of such an instrument. In this case, the surgical planner may define three planes and coordinate systems: the AP plane and coordinate system, the ipsilateral hemipelvic plane and coordinate system, and a registration instrument plane and coordinate system. The registration instrument plane and coordinate system may coincide with a top surface of the registration instrument having one or more legs of different lengths.

In an embodiment, an acetabular template may be used instead of the HipSextant instrument to register the patient's pelvis. For example, the template may be fabricated so that, when docked or attached to the patient's acetabulum, the template defines a coordinate system, such as the ipsilateral hemipelvic plane coordinate system. The surgical plan, moreover, may include a translation function for translating points or vectors from the ipsilateral hemipelvic plane coordinate system to the AP plane coordinate system or some other standard coordinate system. With the template docked or attached to the patient's acetabulum, one or more, and preferably three or more (non-collinear), points on the template may be digitized using the digitizing probe to register the pelvis, e.g., to capture the ipsilateral hemipelvic plane coordinate system and thereby also the anterior pelvic plane coordinate system by the tracking system. Further, instead of digitizing three points on the template, a tracker may be attached to the template in a known, pre-determined way. If that is done, the relationship between the tracker and the template would instantly allow for calculation of the relationship between the tracker and the anterior pelvic plane coordinate system directly, for example by the tracking system 202.

Robotic Procedure

Figure 6:
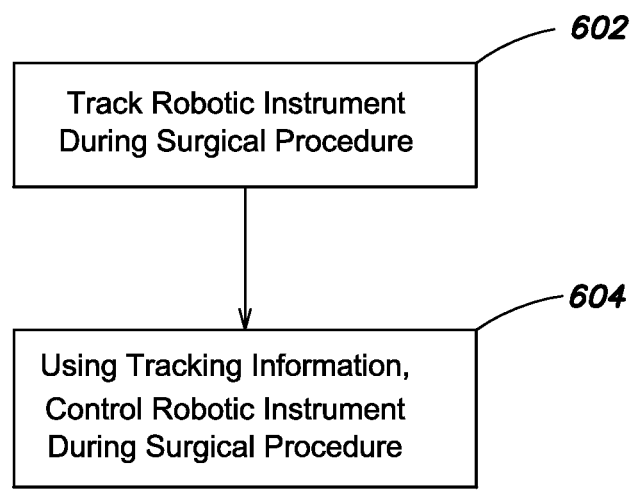
FIG. 6 is a flow diagram of a method in accordance with an embodiment of the present invention.

With the patient's pelvis 214 registered in the operating room 200, a robotically controlled instrument 220 may be used during the surgical procedure. For example, an acetabular reamer instrument may be used to remove that volume or portion of bone or other material specified in the surgical plan, such as a volume of bone at or around the patient's acetabulum. FIG. 6 is a flow diagram of a method in accordance with an embodiment of the present invention. One or more trackers, such as tracker 222, may be attached to the reamer. Specifically, the one or more trackers may be attached to the reamer in a known spatial relationship to the operating tip, e.g., the drill point, of the reamer. The tracking system 202 may be configured to track the position of the drill point as the reamer is used by the surgeon to remove the particular volume or portion of bone specified in the surgical plan, thus creating the desired shape, as indicated at block 602.

In particular, the robotic instrument controller 204 may continuously receive position information from the tracking system 202 as the reamer is moved, e.g., in the surgical field by the surgeon. Using the continuously received position information, the robotic instrument controller 204 may control the operation of the reamer, as indicated at block 604. For example, when the surgeon brings the reamer into a position at the patient's acetabulum where bone is to be removed according to the surgical plan, the controller 204 may engage the reamer. If the reamer is moved away from the region specified in the surgical plan, or has reached a point at which no additional bone is to be removed, the controller may disengage the reamer. In an embodiment, the controller 204 may engage and disengage the reamer by controlling the power to the reamer. For example, if the reamer is electrically powered, the controller may control an electrical power switch on the reamer. The controller 204 may operate the power switch through a wireless or wired link to the reamer. If the reamer is pneumatically powered, the controller may control a pneumatic element, such as a pump, switch or valve.

In another embodiment, instead of controlling power to the surgical instrument, the robotic instrument controller 204 may control the instrument in other ways. For example, the reamer may include a sheath that covers the drill tip or other working portion of the reamer. The robotic instrument controller 204 may operate the sheath, for example retracting the sheath when the drill tip is in a position to remove the portion or volume of bone specified in the plan, and extending the sheath when the drill tip is not in such a position.

In addition to controlling one or more instruments, the tracking system 202 and surgical plan viewer 206 may provide information to the surgeon during the procedure. More specifically, one or more trackers may be attached to an instrument (not shown) used to place the acetabular cup component into the patient's acetabulum. The tracking system 202 may be configured to track the location of the instrument, and to provide that information to the surgical plan viewer 206. Utilizing the patient-based ipsilateral hemipelvic coordinate system and the translation function for translating to the AP plane coordinate system, the surgical plan viewer 206 may compute one or more values, such as flexion and abduction values for the instrument and/or cup component itself with reference to the anterior pelvic plane. The surgical plan viewer 206 may provide a graphical user interface (GUI) on a display, and may present the computed values, e.g., flexion and abduction, in the GUI.

Figure 7:
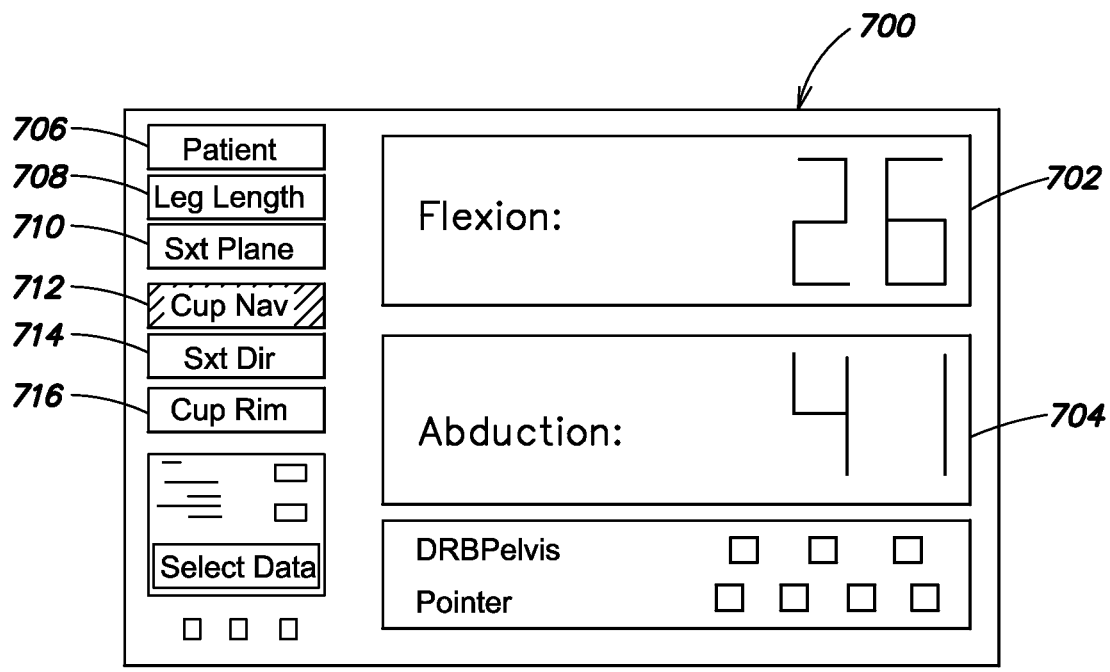
FIG. 7 is a schematic illustration of a user interface in accordance with an embodiment of the present invention.

FIG. 7 is a schematic illustration of a cup navigation GUI 700. The GUI 700 may include a first display element 702 for displaying flexion. The first display element 702 may provide a numerical value for the computed flexion. The GUI 700 also may include a second display element 704 for displaying abduction. The second display element 704 may provide a numerical value for the computed abduction. The flexion and abduction values may be updated in real-time. The cup navigation GUI 700 may be a touch screen, and may include a plurality of menu commands. For example, the GUI 700 may include a Patient command 706, a Leg Length command 708, a HipSextant (Sxt) plane command 710, a Cup Navigation (Nav) command 712, a Sxt Direction (Dir) command 714, and Cup Rim command 716, that may be selected, e.g., by the surgeon or other user. The Sxt Dir may refer to a measurement of an orientation vector of an acetabular cup component. The Cup Rim command may be used to digitize a plurality of points on the rim of the patient's acetabulum, calculate a best fit plane and from the plane a vector that is perpendicular to the plane, which may provide the orientation of the acetabulum cup component.

In response to the selection of a menu command, such as Leg Length command 708, the surgical plan viewer may switch the GUI to a different presentation.

Figure 8:
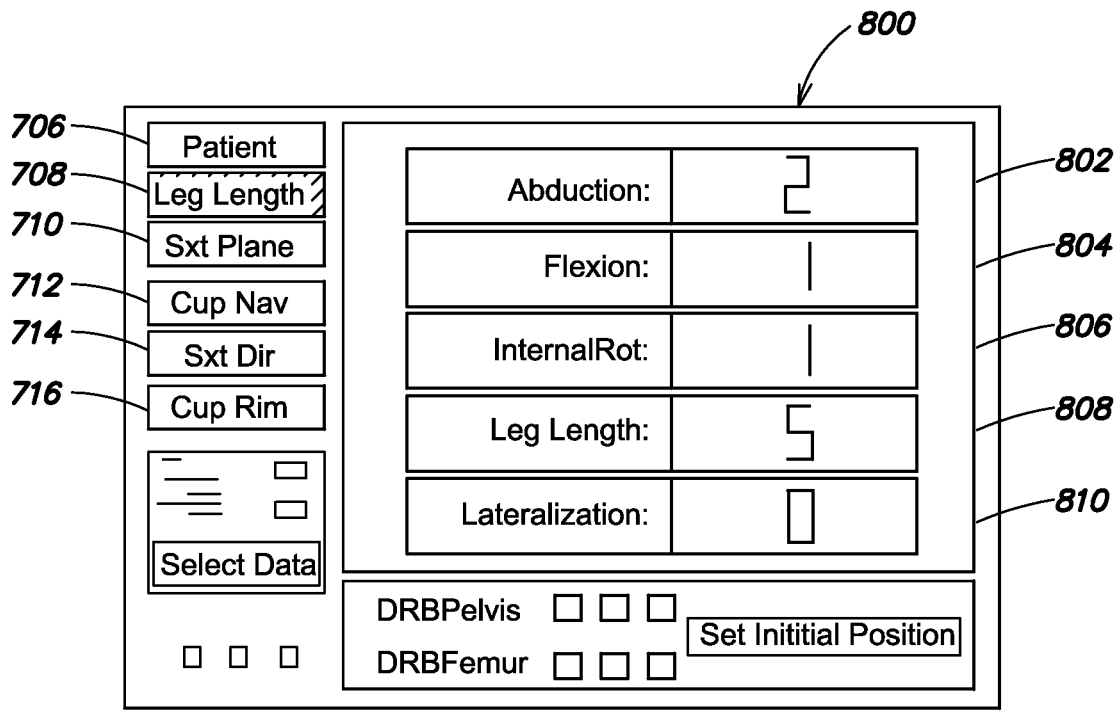
FIG. 8 is a schematic illustration of a user interface in accordance with another embodiment of the present invention.

FIG. 8 is a schematic illustration of a leg length GUI 800. The leg length GUI 800 may include an abduction display element 802, a flexion display element 804, an internal rotation (Rot.) display element 806, a leg length display element 808, and a lateralization display element 810. The leg length GUI 800 also may include the above-described commands 706-716

The foregoing description has been directed to specific embodiments of the present invention. It will be apparent, however, that other variations and modifications may be made to the described embodiments, with the attainment of some or all of their advantages. For example, the robotic instrument controller may be adapted to control other surgical instruments besides the reamer. In addition, different combinations of embodiments may be created. For example, a registration instrument with a zigzag leg and at least one leg having a different length may be created. Such a registration instrument may establish two coordinate systems, e.g., a first coordinate system defined by the tips of the legs, and a second coordinate system defined by the plane established by the top of the instrument, e.g., the top surface of the central hub and arms. Other combinations of different features is also possible. Therefore, it is the object of the appended claims to cover all such variations and modifications as come within the true spirit and scope of the invention.

What is claimed is:

1. A computer-implemented method, comprising:
registering a portion of a patient's anatomy, to be operated on, to a patient-specific coordinate system, the registering performed by (1) placing a plurality of different points of a single physical device simultaneously in direct contact with different surface points on a surface of the patient's anatomy and (2) capturing a coordinate system from the single physical device mated to the patient's anatomy;
continuously tracking, by a processor, one or more positions of a robotic controlled instrument relative to the patient-specific coordinate system as the robotic controlled instrument moves in relation to the portion of the patient's anatomy; and
automatically engaging and disengaging operation of the robotic controlled instrument based on the continuously tracked positions relative to the patient-specific coordinate system.

2. The computer-implemented method of claim 1, wherein the single physical device is a template that is custom-fabricated to fit to the patient's anatomy.

3. The computer-implemented method of claim 1, wherein the portion of the patient's anatomy is a pelvis, and the single physical device is a template that is custom-fabricated to fit to an acetabulum of the patient's pelvis.

4. The computer-implemented method of claim 1, wherein the automatically engaging and disengaging operation of the robotic controlled instrument includes at least one of
turning the robotic controlled instrument on and off,
controlling power to the robotic controlled instrument, or
extending and retracting a protective sheath of the robotic controlled instrument.

5. The computer-implemented method of claim 1, further comprising:
defining, preoperatively, at least one of an orientation or a location of an implant at the portion of the patient's anatomy relative to the patient-sprecific coordinate system, wherein the implant is an acetabular cup component.

6. The computer-implemented method of claim 5, wherein
the portion of the patient's anatomy includes an acetabulum,
the robotic controlled instrument is a reamer, and
the reamer is controlled to shape the acetabulum to receive the acetabular cup component.

7. The computer-implemented method of claim 1, wherein
the robotic controlled instrument is a reamer, and
the one or more positions of a robotic controlled instrument include one or more positions of a drill point of the reamer.

8. The computer-implemented method of claim 1, wherein the robotic controlled instrument is a reamer.

9. The computer-implemented method of claim 1, wherein the single physical device defines a pelvic plane.

10. The computer-implemented method of claim 1, further comprising undocking the single physical device from the patient's anatomy prior to the continuously tracking the one or more positions of the robotic controlled instrument.

11. A method, comprising:
determining a patient-specific coordinate system for a portion of a patient's anatomy to be operated on;
registering the portion of the patient's anatomy to the patient-specific coordinate system, the registering performed using (1) a single physical instrument having a plurality of different physical points that directly contact different surface points of the portion of the patient's anatomy or (2) a single virtual instrument having a plurality of different virtual points that virtually mate directly with the portion of the patient's anatomy;
continuously tracking, by a processor, positions of a robotic controlled instrument relative to the patient-specific coordinate system as the robotic controlled instrument moves near the portion of the patient's anatomy;
automatically engaging and disengaging operation of the robotic controlled instrument based on the continuously tracked positions relative to the patient-specific coordinate system; and
utilizing the patient-specific coordinate system to at least one of
orient, or
locate
an implant at the portion of the patient's anatomy.

12. The method of claim 11, wherein the patient-specific coordinate system defines at least one of an anterior pelvic (AP) plane or an ipsilateral hemipelvic plane.

13. The method of claim 11, wherein the registering is performed using the single physical instrument and the single physical instrument is a template that is custom-fabricated to fit to the patient's anatomy.

14. The method of claim 11, wherein the registering is performed using the single physical instrument and the physical instrument has legs with tips that contact a surface of the patient's anatomy.

15. A method, comprising:
registering a portion of a patient's anatomy, to be operated on, to a patient-specific coordinate system by docking a physical instrument to the patient's anatomy;
continuously tracking, by a processor, one or more positions of a robotic controlled instrument relative to the patient-specific coordinate system as the robotic controlled instrument moves in relation to the portion of the patient's anatomy, wherein the physical instrument is undocked from the patient's anatomy prior to and while the one or more positions of the robotic controlled instrument are continuously tracked relative to the patient-specific coordinate system; and
automatically engaging or disengaging operation of the robotic controlled instrument based on the continuously tracked positions relative to the patient-specific coordinate system.

16. The method of claim 15, further comprising:
defining, preoperatively, at least one of
an orientation, or
a location
of an implant at the portion of the patient's anatomy relative to the patient-specific coordinate system; and
placing the implant at the portion of the patient's anatomy according to the at least one of
the orientation, or
the location.

17. The method of claim 16, wherein the implant is an acetabular cup component.

18. The method of claim 16, further comprising:
creating, preoperatively, a surgical plan, wherein the surgical plan includes
the patient-specific coordinate system, and
the at least one of
the orientation, or
the location
of the implant.

19. The method of claim 15, wherein
the portion of the patient's anatomy includes an acetabulum,
the robotic controlled instrument is a reamer, and
the reamer is controlled to shape the acetabulum to receive an acetabular cup component.

20. The method of claim 15, wherein the registering further includes:
digitizing a plurality of points on the physical instrument.

21. The method of claim 15, further comprising:
tracking, by the processor, a surgical instrument that installs an implant;
computing, based on the tracking the surgical instrument that installs the implant, at least one of a location or an orientation of the implant relative to the patient-specific coordinate system; and
presenting the at least one of the location or the orientation on a user interface.

22. The method of claim 21, wherein the at least one of the location or the orientation is updated in real time on the user interface.

23. The method of claim 21, wherein the at least one of the location or the orientation includes one or more flexion values and one or more abduction values.

24. The method of claim 15, wherein the automatically engaging and disengaging operation of the robotic controlled instrument includes at least one of
turning the robotic controlled instrument on and off,
controlling power to the robotic controlled instrument, or
extending and retracting a protective sheath of the robotic controlled instrument.

25. The method of claim 15, wherein the physical instrument defines at least one of an anterior pelvic (AP) plane or an ipsilateral hemipelvic plane.

* * * * *